(12) United States Patent
Gramann et al.

(10) Patent No.: US 8,449,294 B2
(45) Date of Patent: May 28, 2013

(54) DENTAL IMPRESSION TRAY

(75) Inventors: Jens Gramann, Munich (DE); Robert Oppolzer, Kaufbeuren (DE); Ingo W. Wagner, Wörthsee (DE); Urs Mahnel, Bad Tölz (DE)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 12/514,022

(22) PCT Filed: Sep. 20, 2007

(86) PCT No.: PCT/EP2007/008201
§ 371 (c)(1),
(2), (4) Date: Feb. 12, 2010

(87) PCT Pub. No.: WO2008/055563
PCT Pub. Date: May 15, 2008

(65) Prior Publication Data
US 2010/0151408 A1 Jun. 17, 2010

(30) Foreign Application Priority Data
Nov. 9, 2006 (GB) .................................. 0622247.5

(51) Int. Cl.
*A61C 9/00* (2006.01)
(52) U.S. Cl.
USPC .......................................................... 433/37

(58) Field of Classification Search
USPC ...................................... 433/37–48; D24/181
See application file for complete search history.

(56) References Cited

U.S. PATENT DOCUMENTS

| 1,094,203 | A |  | 4/1914 | Eaton |
| 3,834,025 | A |  | 9/1974 | Schunemann |
| 4,484,890 | A |  | 11/1984 | Jouvin |
| 4,763,791 | A | * | 8/1988 | Halverson et al. .............. 433/37 |
| 4,907,966 | A |  | 3/1990 | Kesling |
| 5,336,086 | A | * | 8/1994 | Simmen et al. ................. 433/37 |
| 6,457,973 | B1 |  | 10/2002 | Fetz et al. |
| 7,021,929 | B2 |  | 4/2006 | DiMarino et al. |
| 2005/0221254 | A1 |  | 10/2005 | Kohani |

FOREIGN PATENT DOCUMENTS

| CH | 497 892 | 10/1970 |
| DE | 199 56 103 | 5/2001 |
| DE | 202 18 063 | 2/2003 |
| FR | 432 533 | 12/1911 |
| FR | 473 090 | 12/1914 |
| GB | 423 534 | 2/1935 |
| GB | 792 070 | 3/1958 |

* cited by examiner

*Primary Examiner* — Heidi M Eide
(74) *Attorney, Agent, or Firm* — Carlos M. Téllez; 3M Innovative Properties Company

(57) ABSTRACT

A dental impression tray is provided having a wall including at least one retaining element. The retaining element at least partially overhangs an associated passageway, wherein the passageway extends between first and second wall surfaces that face in different directions Further, methods and molds to form a dental impression tray according to the invention are provided and a kit including a plurality of such dental impression tray.

18 Claims, 14 Drawing Sheets

DENTAL IMPRESSION TRAY

Cross Reference to Related Applications

This application is a national stage filing under 35 U.S.C. 371 of PCT/EP2007/008201, filed Sep. 20, 2007, which claims priority to Application No. GB 0622247.5, filed Nov. 9, 2006, the disclosure of which is incorporated by reference in its/their entirety herein.

FIELD OF THE INVENTION

The present invention relates generally to dental impression trays and, more specifically, to dental impression trays having retaining elements for retaining a dental impression material within such trays. Furthermore the invention is related to methods and molds for manufacturing a dental tray according to the invention and a kit comprising such a tray.

BACKGROUND OF THE INVENTION

Dental impression trays are used to create negative reproductions of a patient's teeth. These reproductions are generally used to cast models, for example, as is often required for making dental restorations such as crowns and bridges. To take an impression, the dental impression tray is usually filled with a flowable impression material, and then the tray is placed in the patient's mouth and pressed against the teeth. The impression material solidifies while the tray remains in the patient's mouth. As soon as the impression material has become solid, the tray is peeled away from the teeth and removed from the patient's mouth. Plaster or another flowable material is then poured into the solidified impression material to form the model of the patient's teeth.

Because the impression material flows around the teeth and then solidifies, it can be difficult to remove from the teeth even when significant force is applied to the tray. In some cases, the force applied to the tray separates the impression material from the tray rather than from the teeth, which means that the impression material must be separately peeled away from the teeth, and the accuracy required for dental impressions gets lost. This is inconvenient for the patient and the dentist because it tends to render the impression unusable, and as a result the procedure must be done again. The force required to separate the impression material from the tray should therefore be greater than the force required to separate the impression material from the teeth.

Traditionally, a dental adhesive is used to bond the dental impression material to the dental impression tray. Such dental adhesive can be, for example, a polyvinyl siloxane adhesive available from 3M ESPE AG, Germany under the designation VPS Tray Adhesive. The adhesive is first applied to the inner surface of the tray, where it must dry, typically for 3 to 6 minutes. Then the impression material is filled into the tray. Because in a dental practice time is often at a premium, it would be useful to reduce or eliminate the time required for adhesive application and drying if possible.

US 2003/0180680 discloses a dental impression tray comprising a retainer for the dental material. The retainer comprises loop-shaped anchoring elements which are connected to the inner surface of the tray. The retainer, for example, may be the loop part of a hook and loop mechanical fastener, or a non-woven textile material that is fixed to a surface of the tray. Impression material received in the tray is supposed to be anchored at the tray by the mechanical fastener as soon as the impression material has hardened.

U.S. Pat. No. 5,336,086 describes a dental tray having outer and inner walls and a base between the outer and inner walls. The outer and inner walls each comprise vertical slits having a shoulder within each slit, providing an interlock for the impression material that is squeezed through the slit. The base also has holes with a shoulder around the bottom side of each hole. Reservoirs associated with the holes are formed at the bottom of the base and surround the holes so that a relatively large amount of excess impression material that may be in the tray can flow through the holes into the reservoirs, and when solidified, retains the material when the tray is removed from a patient's teeth.

U.S. Pat. No. 7,021,929 relates to a dental impression tray having a plurality of projections and panels on its tray walls, all of which define grooves. Upon taking an impression, dental impression material flows into the grooves to form retentive components. These retentive components may prevent the impression material from distorting or being lifted out of the tray when the tray is disengaged from the teeth of the patient.

In EP 1 029 514 a dental impression tray is described as having an upper portion for holding the impression material, and a lower portion which is defined in the specification as "means for laterally displacing excess impression material." The base of the upper portion has vent holes which force excess impression material to extrude toward the "means for laterally displacing excess impression material." Excess material extruded from the holes interlocks with the excess material extruded from other nearby holes, thereby attaching the impression material to the tray. The tray further comprises a serpentine stop ridge which prevents the patient's teeth from contacting the base of the upper portion of the tray.

In DE 100 04 415 a dental impression tray with retaining elements for the impression material is disclosed. The retaining elements are integrally formed protrusions on a bottom portion of the tray. The retaining elements generally protrude in the direction from which the tray is pulled from a patient's teeth. To increase the retention force the retaining elements are supposed to provide, the protrusions are generally mushroom-shaped, meaning that they have an expanded free end.

Generally it takes some effort to manufacture dental trays with integrated retaining elements, because several manufacturing steps are often necessary. Furthermore, there is often a tradeoff between providing an effective retainer system, providing an easy-to-use tray and achieving inexpensive manufacturing.

SUMMARY OF THE INVENTION

As described it is generally desired to provide for retention of a solidified impression material in a dental tray and to overcome at least some of the disadvantages of the prior art.

A first aspect of the invention is related to a dental impression tray having a wall comprising at least one retaining element. The retaining element at least partially overhangs an associated passageway, wherein the passageway extends between first and second wall surfaces. The wall surfaces preferably face in different directions.

Preferably the dental impression tray comprises a plurality of retaining elements each associated with a passageway. The following description generally refers to a singular "retaining element" and "passageway," but shall include embodiments in which a plurality of "retaining elements" or "passageways" are present.

The term "overhang" is related to a general arrangement of a retaining element relative to a passageway, in which the retaining element is arranged outside of the passageway but a projection of at least a part of the retaining element onto the plane of one of the wall surfaces at least partially overlaps an open end of the passageway. Preferably such a projection is a perpendicular projection onto the plane of one of the wall surfaces. For example, in one embodiment at least one of the retaining elements may cover the open end of the associated passageway at a distance from the open end.

Preferably the first and second wall surfaces face away from one another, and preferably face in generally opposite or preferably in opposite directions. In other words, the first and second wall surfaces are preferably parallel but face in opposite directions.

Preferably, the retaining element is connected with the wall of the tray, and more preferably integrally formed or formed in one piece with the wall. The retaining element may also be integrally molded in a single shot with the wall.

The retaining element is preferably arranged closer to the first wall surface than the second wall surface.

In one embodiment the retaining element comprises a base portion protruding from the first wall surface, and a head portion projecting from the base portion. The head portion of such a retaining element is preferably arranged generally perpendicular, more preferably perpendicular to the base portion, wherein the head portion preferably extends generally parallel, more preferably parallel to the first wall surface. The base portion and the head portion of the retaining element may be arranged generally in an L-shape with the head portion overhanging the passageway that is associated with the retaining element. This means that preferably a projection of the head portion onto the plane of the first wall surface at least partially overlaps an open end of the passageway. The head portion may be spaced apart from the passageway, meaning spaced apart from the open end of the passageway and from the plane of the first wall surface.

In a further embodiment the retaining element comprises at least two base portions preferably protruding from the first wall surface. It is preferred that the retaining element of this embodiment is arranged in a manner so as to form a bridge, meaning the head portion extends between the ends of the base portions that are remote from the first wall surface. Preferably the head portion is spaced apart from the passageway, meaning spaced apart from the open end of the passageway and the plane of the first wall surface. Preferably, the base portions and the head portion form a generally U-shaped bridge spanning the passageway associated with the retaining element.

In another embodiment the head portion of a retaining element is inclined with respect to the base portion. Preferably, the head portion in this case extends at an angle relative to the first wall surface, while the base portion protrudes generally perpendicularly, more preferably perpendicularly from the first wall surface. Preferably, the inclination angle of the head portion relative to the base portion is smaller than 90°. Thus, the base portion and the head portion are arranged so that the joint between the portions forms an acute angle. The head portion with the base portion may therefore form a hook, with the head portion at least partially overhanging the passageway associated with the retaining element.

According to another embodiment the base portion(s) and the head portion form a smooth transition with one another and/or merge smoothly or continuously. For example, the base and the head portions may be formed by a curved structure, or in an arc.

In a further preferred embodiment the head portion of a retaining element comprises a retaining surface facing the passageway associated with the retaining element. The retaining surface preferably faces the open end of the passageway. Preferably, the retaining surface corresponds generally in shape to a cross-sectional area of the passageway. In particular, this cross-sectional area is preferably the cross-sectional area of the passageway adjacent the first wall surface. However, it is encompassed that the retaining surface has a different actual shape but a projection of the retaining surface onto the plane of the first wall surface generally corresponds in shape to a cross-sectional area of the passageway.

The passageways each preferably have at least over a part of their length a generally circular, more preferably circular cross-sectional shape. Alternatively, the passageways each have at least over a part of their length a cross-sectional shape generally corresponding to one of a segment of a circle, a rectangle, a triangle, a cross, a U and a V. Other suitable cross-sectional shapes, however, may be used. One or more passageways may have different cross-sectional shapes, for example as mentioned, over their length.

Preferably, the cross-sectional area of at least one passageway is in a range selected from between 0.5 and 10 $mm^2$, between 1 and 6 $mm^2$ and between 2 and 4 $mm^2$. This also means that the lower limits of the different ranges may be combined with any upper limit of these different ranges, for example the ranges specified above encompass a range of between 0.5 and 4 $mm^2$.

Preferably the retaining surface of the retaining element is spaced away from the first wall surface by between 0.5 and 2 mm, preferably by 1 mm. The coverage of the passageway, meaning the perpendicular projection of the retaining surface onto the first wall surface relative to the cross-section of the passageway, is preferably between 85% and 98%, preferably 95%. The cross-section of the passageway is preferably between 1 $mm^2$ and 12 $mm^2$, preferably (3.2 $mm^2$).

Preferably the passageway forms at least a part of a channel through the tray wall, wherein the retaining element covers the passageway without sealing it. This means that a material may flow from an area in front of the tray wall through the passageway to an area behind the tray wall, with the retaining element being arranged within the flow path of the material.

In a preferred embodiment the dental impression tray comprises a reservoir to receive a dental impression material. Preferably, the reservoir is shaped by the tray wall like a trough extending along a U-shape. Although explanations within this specification may be related to a U-shaped tray, other shapes are generally encompassed for all embodiments disclosed. In particular trays having only a partial U-shape for taking impressions of less than all teeth of a patient's jaw are encompassed. Furthermore trays are encompassed having two reservoirs that substantially face away from one another, for example two reservoirs having a common bottom wall with the reservoirs being located on opposite sides of that bottom wall. The reservoir often is filled using a dispensing device like, for example, Pentamix™ 2 available from 3M ESPE AG, Germany. Such a device mixes a two-component impression material and extrudes a pasty mixture continuously in form of a strand. A user of the tray, for example a dental assistant, usually picks up the strand with the tray beginning at an end of the U the reservoir extends along. He or she then usually continuously fills the reservoir all the way along the U. As mentioned, the tray preferably comprises a plurality of retaining elements. The retaining elements are preferably arranged within the reservoir projecting from the bottom wall of the reservoir. Furthermore, the retaining elements may alternatively or additionally project from a side wall of the reservoir. The pasty impression material preferably flows at least partially around the retaining elements. This may happen during filling, or also when the tray is placed into a patient's mouth. In the latter case, the teeth of the patient penetrate into the paste and displace the paste towards the container walls, meaning towards the tray walls. The paste thus is pressed in a direction of the tray walls and is forced toward and flows around the retaining elements. Once the tray is placed in a patient's mouth the impression material solidifies, for example due to curing by a chemical reaction. Preferably, the retaining elements are adapted to anchor the solidified dental impression material to the tray. The arrangement of the head and the base portion(s) of the retaining elements forms an undercut, meaning that a retaining surface of the retaining elements faces generally away from the open side of the reservoir. Portions of the solidified impression material accommodated beneath such undercuts (meaning accommodated between the retaining surfaces and the passageways), thus hinders the removal of the impression material from the tray, for example when the tray is removed from the patient's mouth. Because the impression material is captured beneath the undercut, the area under the undercut is preferably also a capture area. The retaining elements may be uniformly distributed over at least a part of the wall of the tray. The retaining elements may also be arranged in groups of multiple retaining elements with the groups being uniformly or non-uniformly distributed over at least a part of the wall of the tray. For example, with respect to the U-shape the reservoir extends along, the retaining elements may be distributed more densely close to the ends (or legs) of the U-shape, and in the curved part of the U-shape, relative to the density of the retaining elements in other areas of the U-shape.

In a preferred embodiment the dental impression tray is made of plastic. Preferably, the plastic is one of polypropylene, polyethylene, polycarbonate, polyoxymethylene and acrylonitrile-butadiene-styrene. The plastic material may be fiber reinforced. It is preferred that the dental impression tray is made by injection molding.

Preferably, one of the base and the head portion of the retaining elements of the dental impression tray comprises a cross-sectional area of between 0.25 mm$^2$ and 4 mm$^2$, preferably 2 mm$^2$.

In a second aspect the invention is related to a method of forming a dental impression tray. The impression tray has a reservoir bottom and at least one retaining element arranged within the reservoir and at the reservoir bottom, wherein the tray is preferably completely formed by one-shot injection molding. The tray therefore can be entirely molded in a single step or cycle. This means that the mold can be closed, filled with material, and (after the material has become solid) the mold can be opened to remove the finished tray from the mold. It is encompassed that during such a cycle parts of the mold (meaning cores or other movable structures) can be positioned. Further, it is encompassed that material is injected through more than one channel into the mold. Furthermore, different materials may be injected either through different channels. However, the tray is preferably molded from a single material.

In another embodiment of the invention a method of forming a dental impression tray according to the invention is provided, comprising the steps of:
(i) providing a first mold piece having a first mold structure to form the first tray wall surface;
(ii) providing a second mold piece having a cooperative second mold structure to form a passageway;
(iii) positioning the first and second mold pieces; and
(iv) providing a flowable polymeric or polymerizable material into the mold to form a dental impression tray.

Thus, a dental impression tray may be formed which has a wall comprising at least one retaining element at least partially overhanging an associated passageway, wherein the passageway extends between first and second wall surfaces that face in different directions. Preferably the first mold piece has a plurality of first mold structures to form the first tray wall surface or first tray wall surfaces. And the second mold piece preferably has a plurality of second mold structures to form the passageways.

Preferably, the first and second mold structures are protrusions extending from the first and second mold pieces respectively. The mold pieces are preferably arranged generally opposite one another and in a manner that the mold structures meet at their free ends when the mold pieces are positioned. Preferably, first and second mold structures meet at contact surfaces when the mold pieces are positioned in their final position. "Final position" means that the first and second mold structures are in a position allowing for molding the corresponding tray structures in their desired final shape. In particular, the contact surface of the first mold structures are preferably in contact with a side wall of the second mold structures, and the contact surface of the second mold structures are in contact with a side wall of the first mold structures. In this regard the contact surfaces may be side walls of the first and second mold structures, meaning that the first and second mold structures are offset laterally relative to each other but touch at their sidewalls when the mold pieces are positioned. Alternatively the contact surfaces may be front walls of the first and second mold structures. However, in latter case the front faces of the first and second mold structures meet with an edge of the side walls of the second and first mold structures respectively, meaning that first and second mold structures are laterally offset relative to each other and overlap only partially with one another. A front wall in this context is a surface that is generally parallel to surfaces of the mold forming the wall of the tray, and a side wall is a wall generally transverse to the front wall. However, the term "generally parallel" and "generally perpendicular" encompass modified orientations of surfaces in the scope of embodiments providing similar effects.

The side walls of the mold structures may be angled to allow pressing of the contact surfaces together by pushing the mold structures towards one another. This pressure prevents the polymeric or polymerizable material from penetrating between the contact surfaces of the mold structures, which would probably result in improper shaping of the retaining elements and/or passageways of the tray. Preferably, the first and second mold structures comprise additional beveled portions at their free ends forming at least a part of the contact surfaces.

A third aspect of the invention is related to a mold for forming a dental impression tray according the invention. The mold comprises:
(i) a first mold piece having a first mold structure for forming a wall first wall surface of the tray wall;
(ii) a second mold piece having a second mold structure for forming a passageway in the tray wall;
wherein first and second mold structures are adapted to contact at a contact surface with one another when the mold pieces are positioned. Preferably the first mold piece has a plurality of first mold structures to form the first tray wall surface or first tray wall surfaces. And the second mold piece preferably has a plurality of second mold structures to form the passageways.

In an embodiment of the invention a mold for forming a dental impression tray is provided which comprises:
(i) a first mold piece having a mold structure for forming a first wall surface and a first retaining element surface; and (ii) a second mold piece having a mold structure for forming a passageway in the tray wall and a second retaining element surface.

Preferably the first mold piece has a plurality of mold structures for forming a first wall surface or first wall surfaces and for forming first retaining element surfaces.

The second mold piece preferably has a plurality of second mold structures for forming passageways in the tray wall and second retaining element surfaces.

Preferably, the first and the second retaining element surfaces face in different directions. Further it is preferred that the first and second retaining element surfaces complement one another and generally define a retaining element according to the invention.

A fourth aspect of the invention is related to a method of forming a tray according to the invention. In an embodiment the method comprises the steps of:
 (i) providing an at least partially pre-shaped dental impression tray having a passageway; and
 (ii) deforming the area of the pre-shaped dental impression tray adjacent the passageway so as to form a retaining element.

Preferably the method comprises the steps of providing an at least partially pre-shaped dental impression tray having passageways, and deforming the areas of the pre-shaped dental impression tray adjacent the passageways so as to form retaining elements.

In a preferred embodiment of the invention the method comprises the steps of
(i) providing a blank;
(ii) creating within the blank at least one incision along an open contour; and
(iii) deforming an area of the blank adjacent the incision so as to displace the area relative to the other areas of the blank, thereby forming a passageway in the blank, and wherein the displaced area at least partially forms a retaining element.

Preferably this method comprises creating a plurality of incisions to form passageways and retaining elements by at least the steps mentioned.

The blank may be any deformable material like plastic material as mentioned above. Preferably the blank is made of metal, in particular the blank may be made of V2A (EN Standard Steel no. 1.4301) or V4A (EN Standard Steel no. 1.4571). The deformation may be performed by cold or hot forming.

A fifth aspect of the invention is related to a kit, comprising a plurality of dental impression trays according to the invention. The dental impression trays have different sizes adapted to fit a variety of patients and clinical situations. Further a kit may be provided comprising a dental impression tray and a dental impression material.

The dental impression tray may be used with the following impression materials: Position™ Penta™, Palgat™ Plus™, Impregum™ Penta™, Impregum™ F, Express™ Penta™ Putty, Express™, Express™ Penta™ H, Imprint™ II Garant™ as available from 3M ESPE AG, Germany.

Further aspects and embodiments of the present invention are recited in the appended claims.

The dental impression tray according to the invention can preferably be molded in one step with the advantage that at the same time a retaining function for the dental impression material is provided, as opposed to having to provide an adhesive or other retaining system separately. Furthermore, the user of the tray, for example the dentist's assistant, does not have to prepare the dental tray to make it usable, for example by coating the inside of the reservoir with an adhesive. However, it would still be possible to use an adhesive together with the tray of the present invention to improve the retention of the impression material in the tray. With respect to recycling of a used tray it is also an advantage that a single material can be used for making the tray.

A further advantage may be provided by the fact that air can escape through the passageway when the impression material flows toward and around the retaining elements, and therefore the solidified impression material can link tightly with the retaining elements without most of the air bubbles that might otherwise be present. It is also a preferred advantage that the impression material flows under the retaining elements before it reaches the passageways, because impression material coming through the passageways indicates to the dentist that the impression material will be adequately retained in the tray. Furthermore, because the passageways provide a bottleneck for the flow of the impression material when the tray is placed on a patient's teeth, pressure is created that forces the material to flow around and near the retaining elements.

BRIEF DESCRIPTION OF THE DRAWINGS

FIG. 15b is a cross-sectional view of a section of a blank or tray wall having a retaining element made by deformation of the protrusion of FIG. 15a.

DETAILED DESCRIPTION OF THE INVENTION

Figure 1:
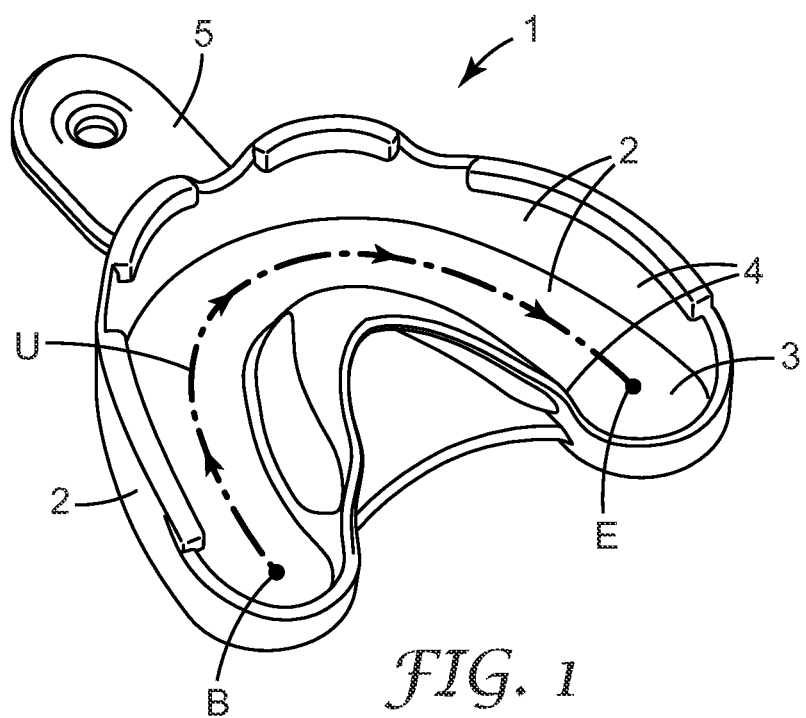
FIG. 1 is a perspective view of an embodiment of a dental impression tray according to the invention with the retaining elements and passageways not shown for better clarity.

FIG. 1 shows the general structure of the dental impression tray 1. For clarity the retaining elements and passageways of the invention are not shown in this view, but different embodiments thereof are explained in detail below. The tray has at least one wall 2, which is typically a bottom wall 3 and tray side walls 4. The tray wall 2 forms a trough-shaped reservoir for receiving dental impression material. The reservoir extends in a U-shape as designated as "U" in FIG. 1. The tray may further comprise a grip 5 by which the tray can be held when used.

To prepare the tray, dental impression material is dispensed into the reservoir, for example, by use of a motorized Pentamix™ 2 dispensing device (not shown) available from 3M ESPE AG, Germany. The tray can also be filled by a syringe or other manually-operated dispensing apparatus. A user, for example a dentist or a dentist's assistant, usually fills the tray by continuously dispensing a pasty impression material into the reservoir along path "U". For example, the user can hold the tray at grip 5 and continuously fill the reservoir beginning from point "B" (the beginning), along the "U" in a direction as indicated by the arrows and stop filling near point "E" (the end), or the reverse. Grip 5 is also commonly used to place the tray into a patient's mouth while the impression material still has a pasty consistency, and to remove the tray from the mouth as soon as the impression material has solidified.

Figure 2A:
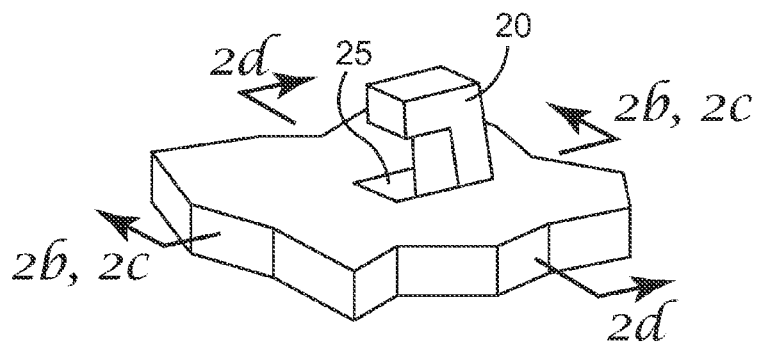
FIGS. 2a-2d are views of a section of a tray wall with a substantially L-shaped retaining element and an associated passageway according to an embodiment of the invention.
Figure 2B:
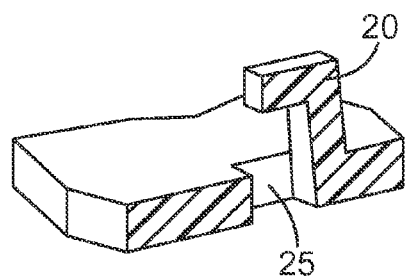
Figure 2C:
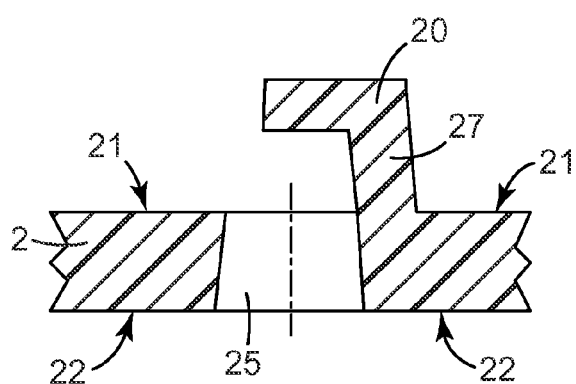
Figure 2D:
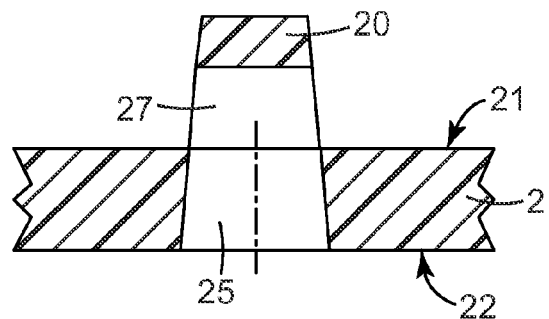

FIGS. 2a-2d show retaining elements and passageways of the type that would be formed in a tray shown in FIG. 1, and in particular they illustrate views of a section of a tray wall 2 with a substantially L-shaped retaining element 20 and an associated passageway 25. FIG. 2a is a perspective view of a portion of a tray wall, which could be a bottom wall or a side wall, with retaining element 20 and passageway 25. FIGS. 2b, 2c and 2d show sections of FIG. 2a as indicated in FIG. 2a. As can be seen in FIGS. 2c and 2d the passageway 25 extends between a first wall surface 21 and a second wall surface 22 so that it ends at first and second wall surfaces 21, 22. The retaining element 20 protrudes adjacent the passageway with a base portion 27 from the first wall surface 21. First and second wall surfaces 21, 22 face away from one another. The retaining element 20 at least partially overhangs the associated passageway 25.

Figure 3:
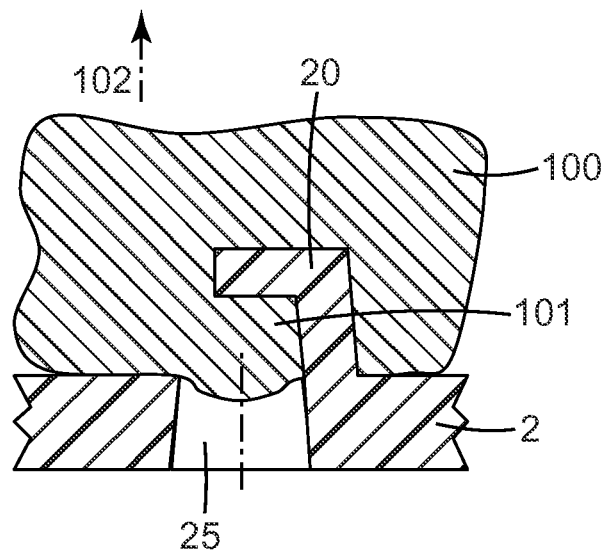
FIG. 3 is a cross-sectional view of a section of a tray wall with dental impression material around a retaining element according to an embodiment of the invention.

FIG. 3 shows the embodiment as illustrated in FIGS. 2a-2d, with a dental impression material 100. When the dental impression material is forced to flow toward the wall 2, for example, because the tray is placed in a patient's mouth and pressed against the teeth, the impression material 100 flows around the retaining elements 20. The impression material also flows into a capture area 101 between the retaining elements 20 and the passageways 25. Retaining elements 20 form an undercut with respect to the direction 102 of the open top of the reservoir. The impression material can fill the capture area 101 under the undercut entirely because air can escape from this area through the passageway 25. Further, complete filling of the capture area is possible because the impression material has to overcome a certain flow resistance to enter the passageway, so that a pressure is built up within the impression material which forces it to fill spaces within the tray. In this way the retaining element is adapted to prevent the solidified impression material from being pulled away from the tray wall, because the impression material when solidified is locked in the capture area by the undercut.

Figure 4:
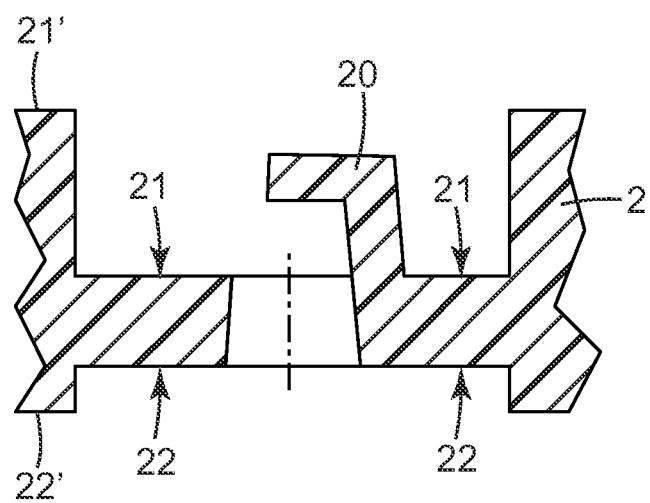
FIG. 4 is a cross-sectional view showing the first and second wall surfaces being recessed relative to outer tray walls according to an embodiment of the invention.

As illustrated in FIG. 4, first and second wall surfaces 21 and 22 are not necessarily the outermost wall surfaces 21' and 22', but may be surfaces of recessed areas in the wall or even embossed areas (not shown) on the wall. However, for example in an embodiment as shown in FIGS. 2a-2d, at least the second wall surface 22 is preferably an outer wall surface. Although the embodiment of FIG. 4 is shown and explained referring to the L-shaped retaining element, other types of retaining elements as described in this specification may be used in combination with the arrangement of the outer, first and second wall surfaces as mentioned in this description of FIG. 4.

Generally, for all embodiments the tray wall may comprise one or more such first and second wall surfaces, meaning that, for example, the wall may comprise one large first wall surface or more than one individual first wall surface. Accordingly, the wall may comprise one large second wall surface or more than one individual second wall surfaces. Furthermore, the first and second wall surfaces may represent the outer wall surfaces or at least a part of them.

Figure 5A:
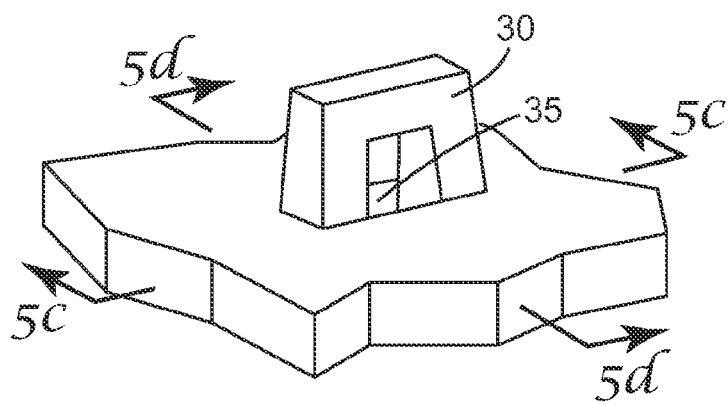
FIGS. 5a-5d are sectional or cross-sectional views of a tray wall with a substantially U-shaped retaining element and an associated passageway according to an embodiment of the invention.
Figure 5B:
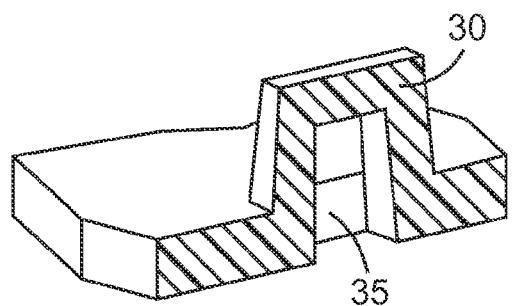
Figure 5C:
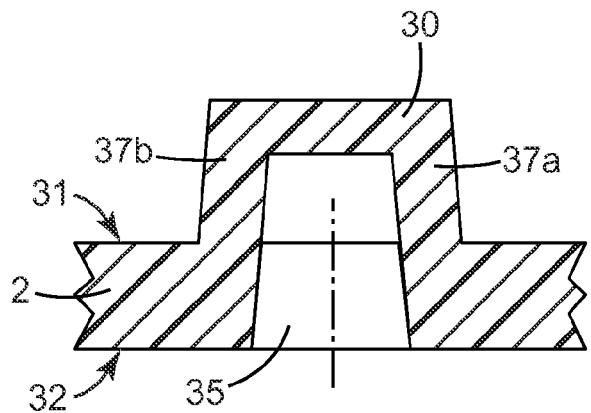
Figure 5D:
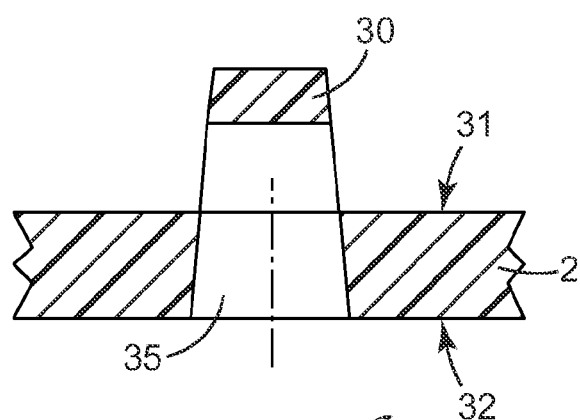

FIGS. 5a-5d show views of a section of a tray wall 2 with a substantially U-shaped retaining element 30 and an associated passageway 35. FIG. 5a is a perspective view of a section of the tray wall with the retaining element 30 and the passageway 35. FIGS. 5b, 5c and 5d show sections of FIG. 5a as indicated in FIG. 5a. The passageway 35 extends between a first wall surface 31 and a second wall surface 32. The retaining element protrudes adjacent the passageway 35 with base portions 37a, 37b from the first wall surface 31. The retaining element 30 bridges the associated passageway 35. First and second wall surfaces 31, 32 face away from one another and particularly are oriented in opposite directions. Again, the first and second wall surfaces are not necessarily the outermost wall surfaces, but may be surfaces of recessed or embossed areas in the wall as described with reference to FIG. 4.

Figure 6A:
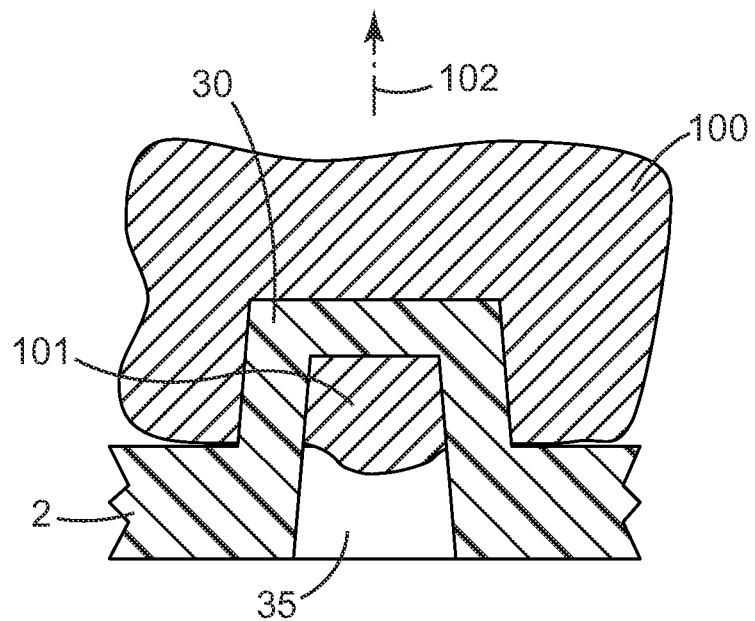
FIG. 6a, 6b are cross-sectional views of a section of a tray wall with dental impression material around a retaining element according to an embodiment of the invention.
Figure 6B:
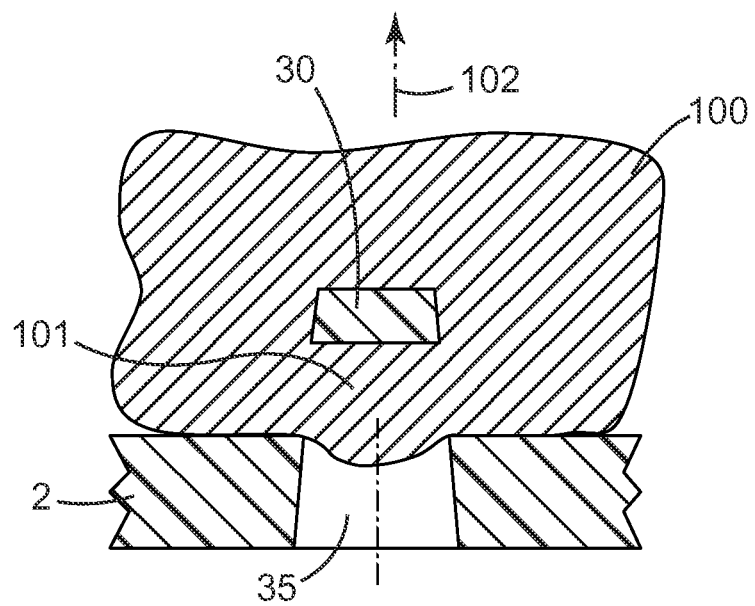

FIGS. 6a and 6b show the embodiment as illustrated in FIGS. 5a-5d, with a dental impression material 100. The retaining elements 30 are arranged like bridges on the wall of the tray that each span a capture area 101. In other words, the retaining elements form first closed structures over a capture area. The capture area 101 adjoins the passageway 35. The impression material can fill the capture area 101 essentially entirely because air can escape from this area through the passageway 35. When the dental impression material is forced to flow toward the wall 2 the impression material 100 flows around the retaining elements 30 and rejoins in the capture area 101. The impression material when solid forms a second closed structure that is interlinked with the first closed structures, like links of a chain. Therefore the retention is provided by two interlinked closed structures—one provided by the retaining element and the other provided by the solid impression material. Thus, a non-detachable connection between the solid impression material and the retaining element is formed, meaning that a detachment of the impression material would only be possible by breaking either the impression material or the retaining element, or both. This retention arrangement is advantageous because the force required to break either the impression material or the retaining element may be quite high, depending on the material(s) used. The solid impression material is therefore tightly held in the reservoir of the tray.

Figure 7A:
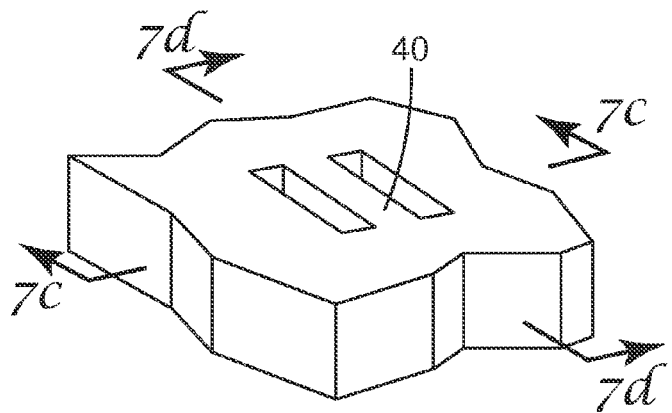
FIGS. 7a-7d are sectional or cross-sectional views of a tray wall with a retaining element formed by intersecting recesses according to an embodiment of the invention.
Figure 7B:
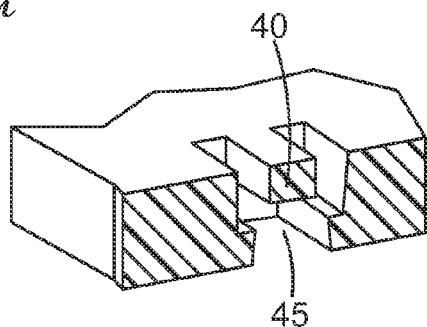
Figure 7C:
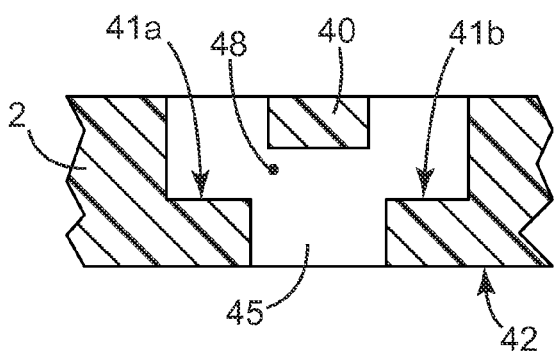
Figure 7D:
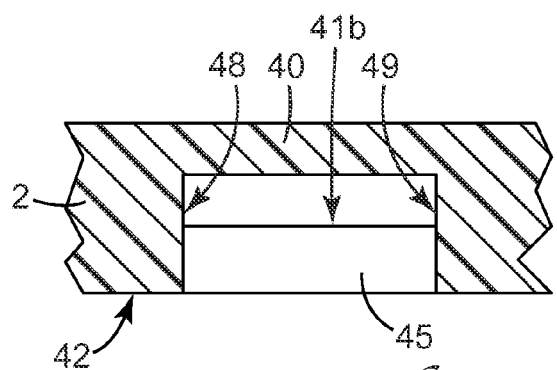

FIGS. 7a-7d show views of a section of a tray wall 2 with a retaining element 40 and an associated passageway 45. FIG. 7a is a perspective view of a section of the tray wall 2 with the retaining element 40 and the passageway 45. FIGS. 7b, 7c and 7d show sections of FIG. 7a as indicated in FIG. 7a. The passageway 45 extends between first wall surfaces 41a, 41b and a second wall surface 42 so that it ends at first and second wall surfaces 41a/41b, 42. The wall 2 comprises a retaining element 40 that bridges the associated passageway 45. In particular, in this embodiment the projection of the retaining element 40 onto the plane of first wall surfaces 41a, 41b at least partially covers the passageway 45. Although not shown, the retaining element may not completely bridge the passageway 45. In this case retaining elements may extend from at least one of the side walls 48, 49 as protrusions having a free end. The first wall surfaces 41a, 41b of this embodiment are recessed relative to an outer wall of the tray. First wall surfaces 41a, 41b face away from the second wall surface 42 and particularly are oriented in opposite directions. The second wall surface 42 may correspond to an outer wall surface as shown. However, it may also, as indicated in FIG. 4, be part of a recessed or even embossed area (not shown).

Figure 8:
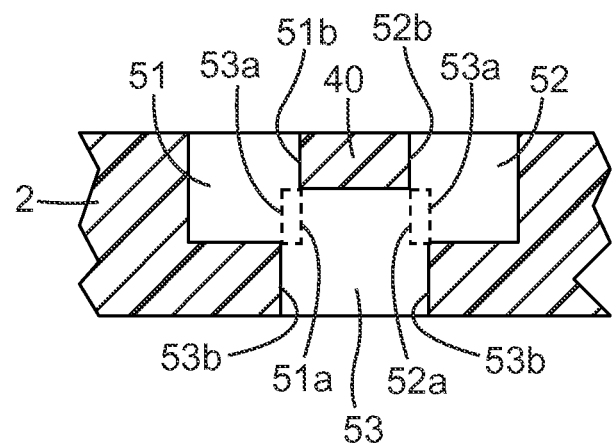
FIG. 8 is a cross-sectional view of FIG. 7a indicating the intersection areas of the recesses.
Figure 9:
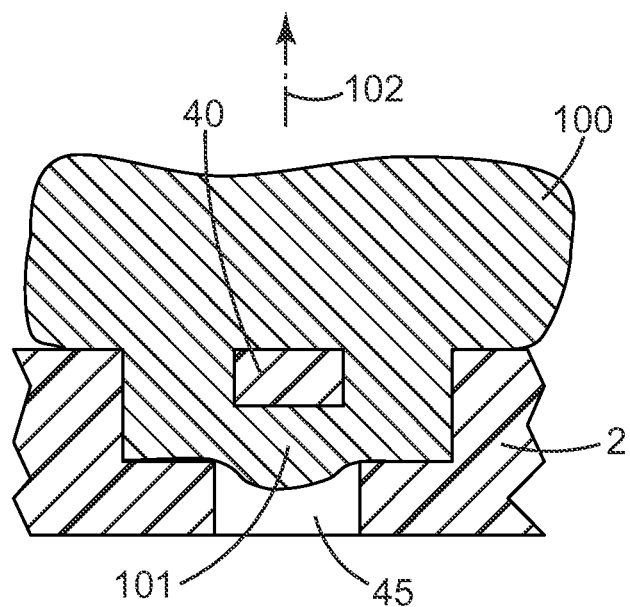
FIG. 9 is a cross-sectional view of a section of a tray wall with dental impression material around a retaining element according to an embodiment of the invention.

The embodiment illustrated in FIGS. 7a-7d can also be described as being formed by first recesses 51, 52 and a second recess 53 (illustrated in FIG. 8). The first recesses 51, 52 extend from one side (in FIG. 8, from the top) into the tray wall 2 and second recesses 53 extend from the opposite side (in FIG. 8, from the bottom) into the wall 2 so that they intersect. The first recesses 51, 52 each intersect with a side wall 53a of the second recess 53, and the second recess 53 intersects with a side wall 51a, 52a of the first recesses 51, 52. In other words, the first recesses 51, 52 overlap partially with the second recess 53, and the second recess 53 partially overlaps the first recesses 51, 52. Thereby a retaining element 40 is formed, and impression material can flow toward and around it to anchor the material to the tray (see FIG. 9). The intersecting or overlapping areas are illustrated in FIG. 8 as dashed lines 51a, 52a and 53a. These lines indicate imaginary continuations of the side walls 51b, 52b and 53b of the recesses 51, 52 and 53.

The embodiment illustrated in FIGS. 7a-7d can also be described as being formed by first recesses 51, 52 and a second recess 53 (illustrated in FIG. 8). The first recesses 51, 52 extend from one side (in FIG. 8, from the top) into the tray wall 2 and second recesses 53 extend from the opposite side (in FIG. 8, from the bottom) into the wall 2 so that they intersect. The first recesses 51, 52 each intersect with a side wall 53a of the second recess 53, and the second recess 53 intersects with a side wall 51a, 52a of the first recesses 51, 52. In other words, the first recesses 51, 52 overlap partially with the second recess 53, and the second recess 53 partially overlaps the first recesses 51, 52. Thereby a retaining element 40 is formed, and impression material can flow toward and around it to anchor the material to the tray (see FIG. 9). The intersecting or overlapping areas are illustrated in FIG. 8 as dashed lines 51a, 52a and 53a. These lines indicate imaginary continuations of the side walls of the recesses 51, 52 and 53.

Figure 10:
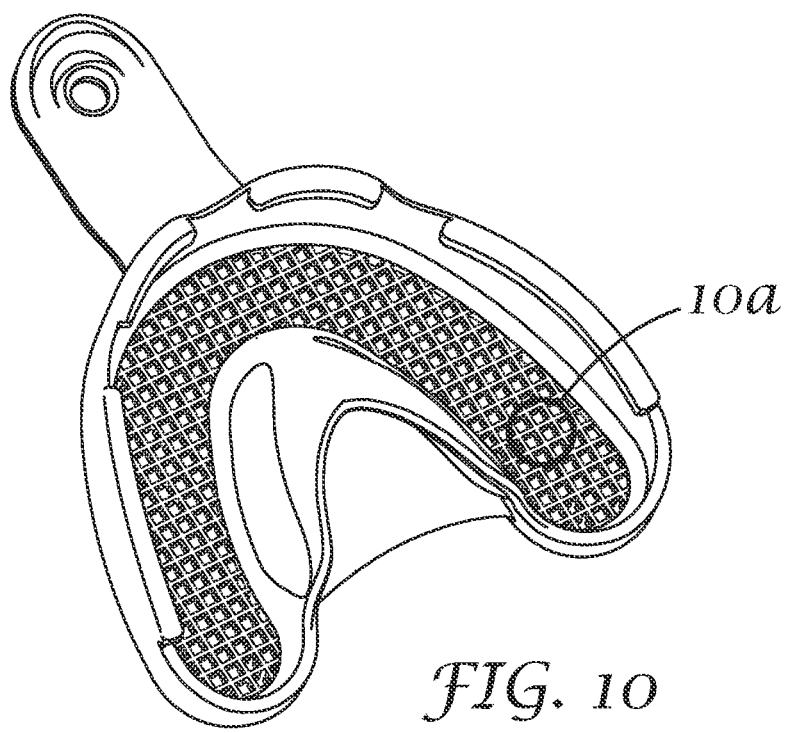
FIG. 10 is a perspective view of a dental impression tray having grouped substantially U-shaped retaining elements according to an embodiment of the invention.
Figure 10A:
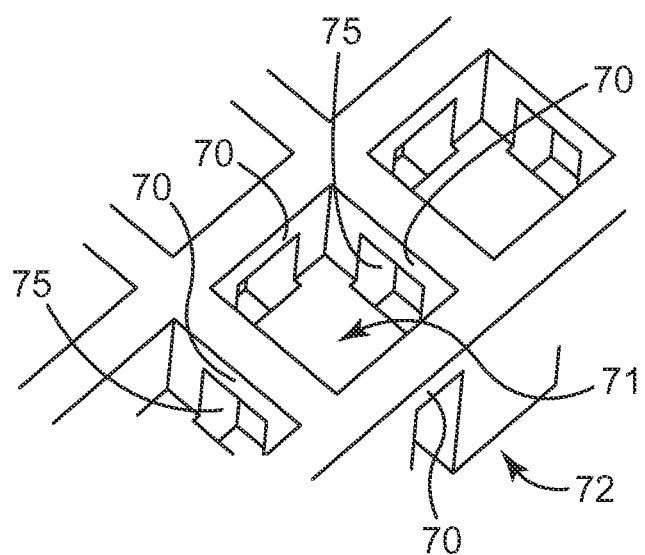
FIG. 10a is a perspective view of an enlarged section of FIG. 10.

FIG. 10 shows a tray 1 having retaining elements 70 that generally have a U-shape, which generally correspond to an embodiment shown in FIGS. 5a-5d. The retaining elements 70, however, are grouped as four retaining elements arranged around a square and connected with one another. Therefore a structure is formed similar to an open room having a door in each of its four walls. The tray wall shown has a plurality of those rooms arranged adjacent to one another (so that the walls form a grid-like structure) and are connected to one another by the doors. The enlarged section in FIG. 10a illustrates passageways 75 that extend between first wall surfaces 71 and a second wall surface 72. The passageways 75 are bridged by the retaining elements 70. The so-called rooms do not need to have the same size, shape, or numbers of doors, and may be arranged in any suitable manner.

Figure 11:
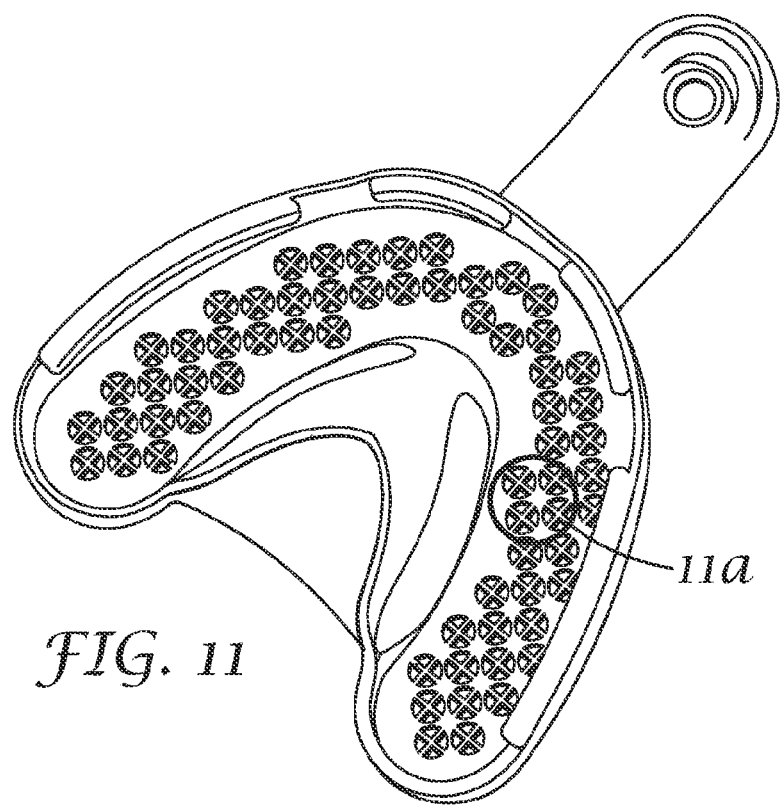
FIG. 11 is a perspective view of a dental impression tray having grouped retaining elements formed by intersecting recesses according to an embodiment of the invention.
Figure 11A:
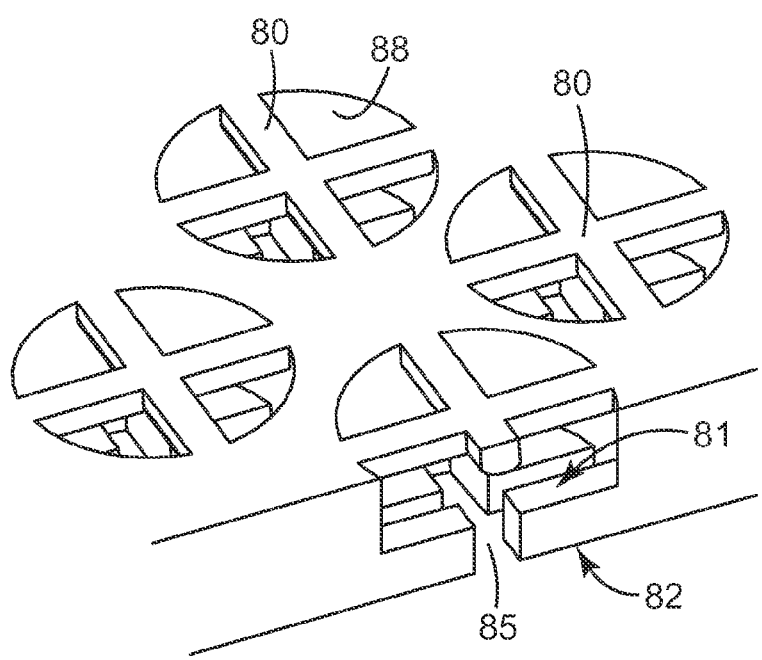
FIG. 11a is a perspective view of an enlarged section of FIG. 11.

FIG. 11 shows a tray having retaining elements 80 which generally correspond to an embodiment shown in FIGS. 7a-7d. However, the retaining elements 80 and the associated passageways 85 are shaped as crosses or (in one section) the negative of crosses, respectively, and the side wall 88 is of a cylindrical shape. The enlarged section in FIG. 11a illustrates retaining elements 80 extending between cylindrical side wall 88. Furthermore, passageways 85 are shown that extend between first wall surfaces 81 and a second wall surface 82 being overhung by the retaining elements 80.

It is generally difficult to mold undercuts in parts because the same structures of the mold that form the undercuts may become locked into those undercuts when molding is complete. Therefore molding of undercuts often requires molds with movable structures that permit the article to be molded, and thereafter can be removed from around such undercuts. Because a tray as it is described above preferably has a plurality of retaining elements each comprising an undercut, a mold with movable parts would be very difficult to make, very expensive and would require significant maintenance. The tray of the invention, however, also provides advantages with regard to the inventive molds and molding processes described below.

Figure 12A:
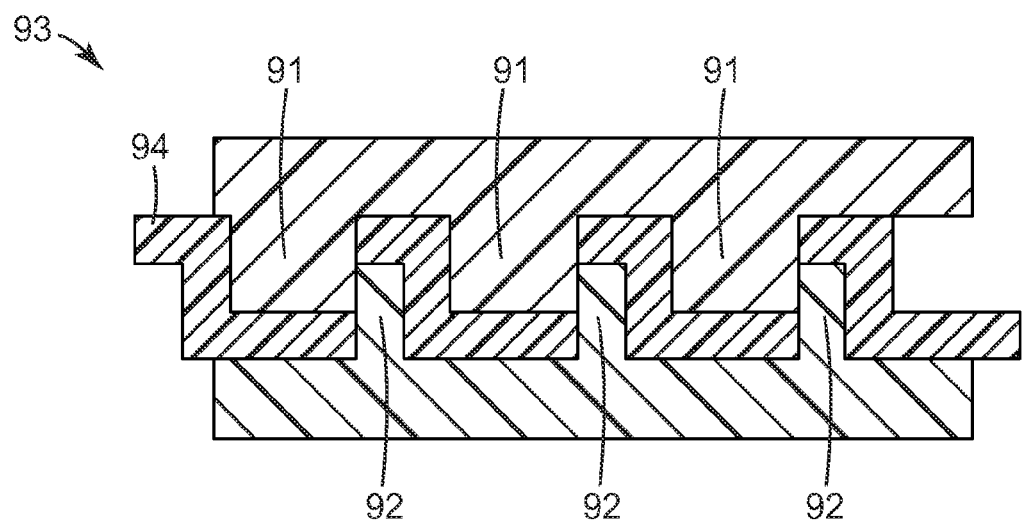
FIG. 12a, 12b are schematic views of mold pieces having first and second mold structures according to an embodiment of the invention.
Figure 12B:
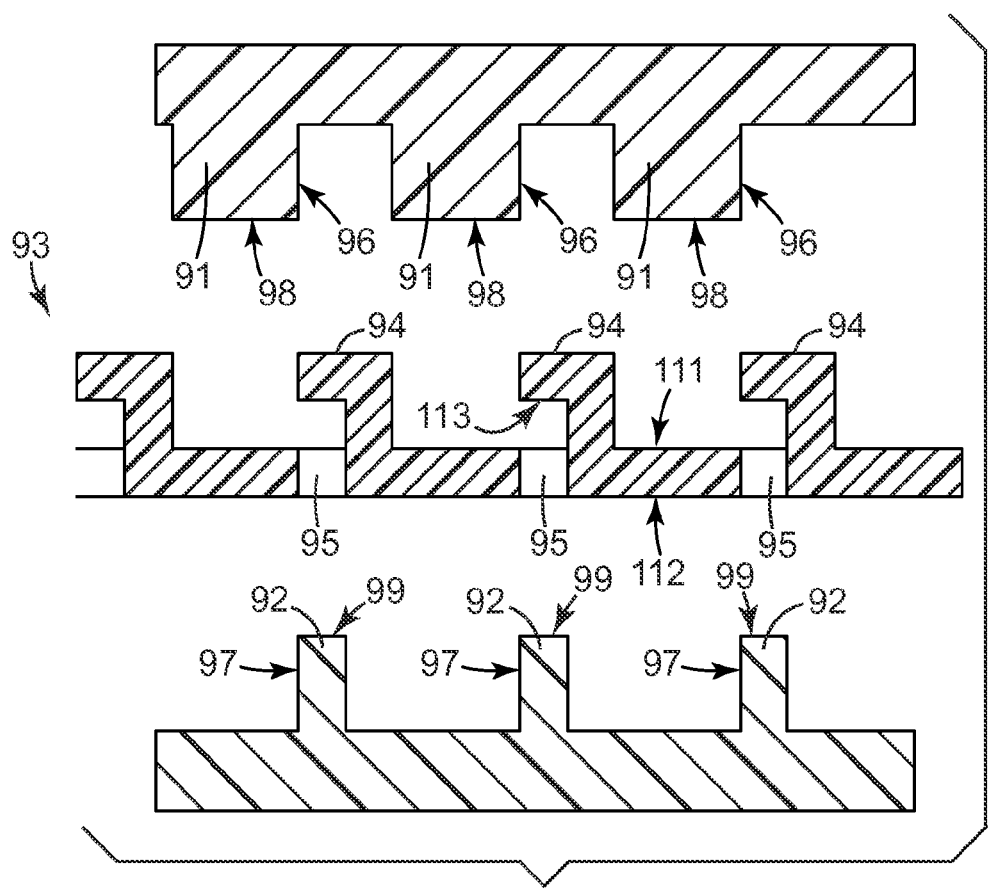

FIG. 12a shows the position of the first and second mold structures 91, 92 when the mold pieces are positioned for molding, whereas FIG. 12b illustrates a position when the mold pieces are moved away from one another so that the tray can be removed from the mold. FIG. 12a and FIG. 12b illustrate mold pieces having first mold structures 91 and second mold structures 92. A part 93 of the tray wall is shown, having retaining elements 94 overhanging associated passageways 95. The passageways extend between first wall surfaces 111 and second Wall surfaces 112. Second mold structures 92 are adapted to form the passageways 95 as well as with their front faces 99 the retaining surfaces 113 of the retaining elements facing the passageways 95. Front faces 98 of first mold structures 91 are adapted to form first wall surfaces 111. In the embodiment shown in FIG. 12a the contact surfaces of the first mold structures 91 are in contact with a side wall 97 of the second mold structures 92, and the contact surfaces of the second mold structures 92 are in contact with a side wall 96 of the first mold structures 91. In this case the contact surfaces correspond to a part of the side walls of the mold structures.

Figure 13A:
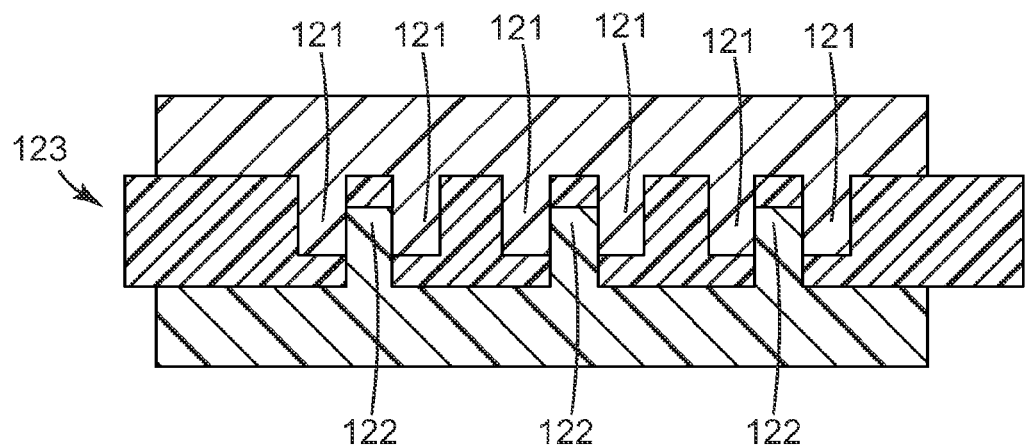
FIG. 13a, 13b are schematic views of mold pieces having first and second mold structures according to an embodiment of the invention.
Figure 13B:
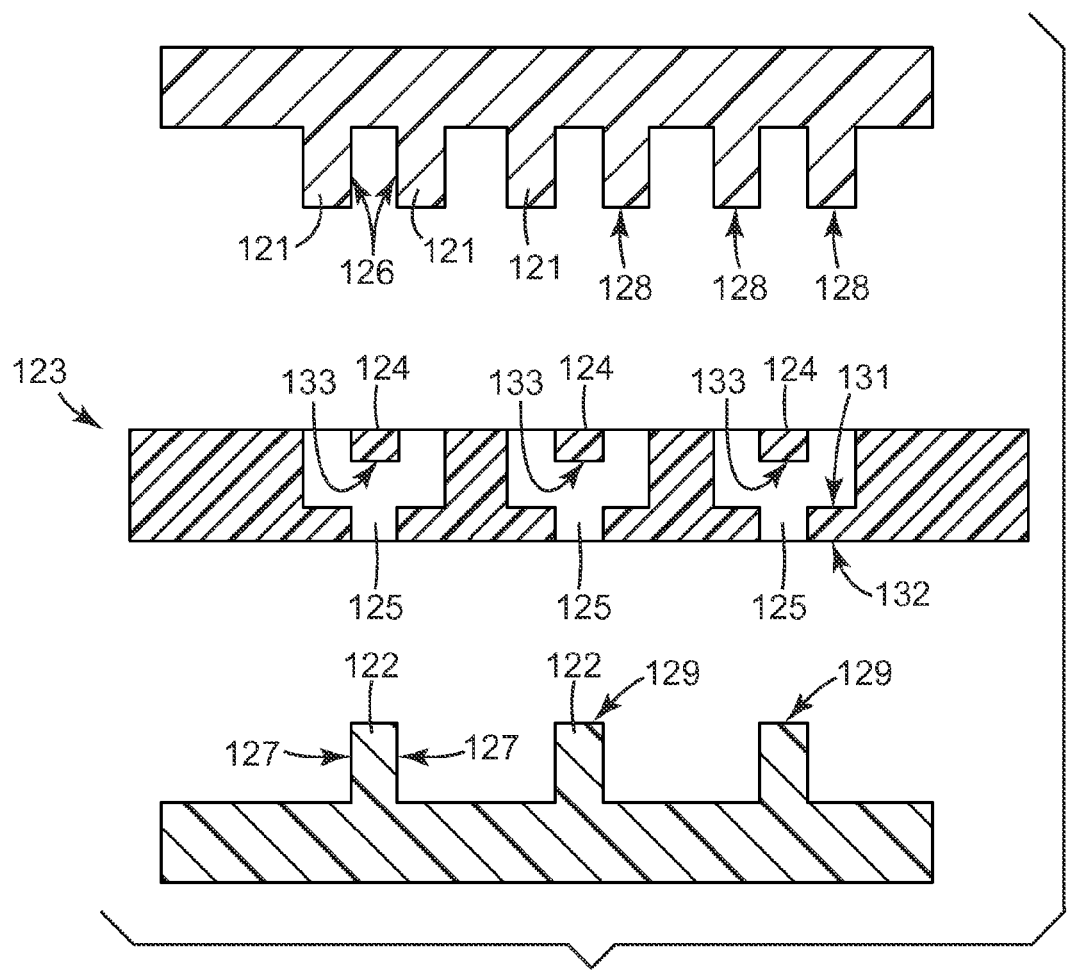

FIG. 13a and FIG. 13b show a mold piece of another embodiment, wherein the mold has first and second mold structures 121, 122. FIG. 13a shows the position of the first and second mold structures 121, 122 when the mold pieces are positioned for molding, whereas FIG. 13b illustrates a position when the mold pieces are moved away from one another so that the tray can be removed from the mold. A part 123 of the tray wall is illustrated with retaining elements 124 overhanging the passageways 125. The passageways 125 extend between first wall surfaces 131 and second wall surfaces 132. In this embodiment the first and second wall surfaces correspond to outer wall surfaces of the tray wall. Front faces 128 of the first mold structures 121 are adapted to form first wall surfaces 131 and second mold structures 122 are adapted to form the passageways 125 and with their front faces 129 to form the retaining surfaces 133 of the retaining elements 124 facing the passageways 125. In the embodiment shown, the contact surface of the first mold structures 121 are in contact with side walls 127 of the second mold structures 122, and the contact surface of the second mold structures 122 are in contact with a side wall 126 of the first mold structures 121. Also in this embodiment the front faces 128, 129 do not overlap with each other.

Figure 14A:
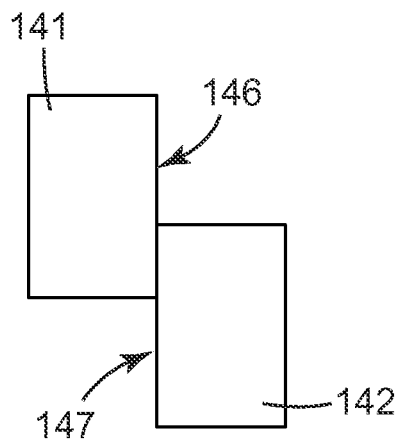
FIGS. 14a-14d are schematic illustrations of exemplary mold structures having contact surfaces according to different embodiments of the invention.
Figure 14B:
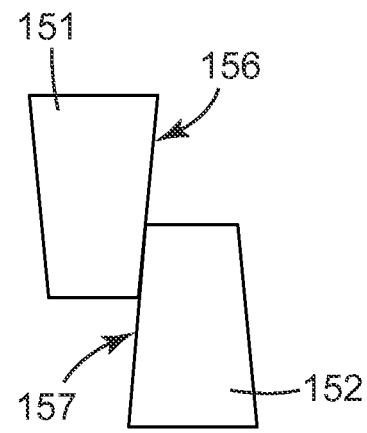
Figure 14C:
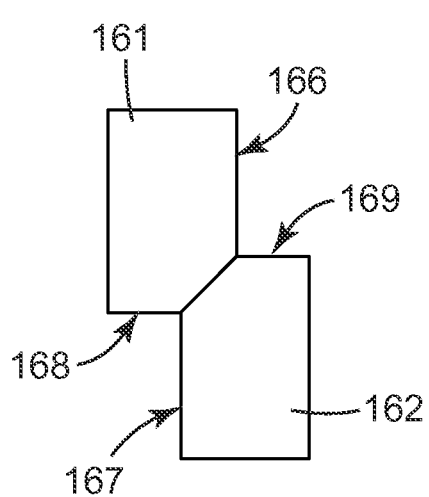
Figure 14D:
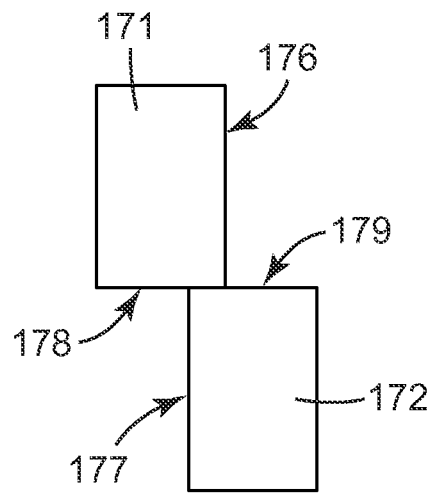

FIG. 14a to FIG. 14d show schematically different embodiments of first mold structures 141, 151, 161 and 171 and second mold structures 142, 152, 162 and 172. FIG. 14a shows an embodiment as previously described for FIGS. 12a/12b and 13a/13b. The first and second mold structures 141, 142 touch each other at side walls 146 and 147 so that the contact surfaces are a part of the side walls 146, 147 of the mold structures 141, 142. In contrast to FIG. 14a, FIG. 14b shows a modified embodiment with first and second mold structures 151, 152 having inclined or tapered side walls. However, also in this embodiment the contact surfaces are formed by a part of the side walls 156, 157 of the mold structures 151, 152. In FIG. 14c first and second mold structures 161, 162 are shown having a beveled portion with respect to the side walls 166, 167 (and with respect to front faces 169, 168). The contact surfaces of this embodiment are formed by the overlapping surfaces of the beveled portions. In particular in the embodiment shown the contact surfaces are formed by the surfaces of the beveled portions. FIG. 14d illustrates an embodiment of first and second mold structures 171, 172 that touch each other at their front surfaces. In this case the contact surfaces are formed each by a part of the front face 178 of the first mold structure 171 and a part of the front face 179 of the second mold structure 172. It can also be seen among all embodiments as illustrated in FIGS. 14a to 14d that the first mold structures 141, 151, 161, 171 are in contact with side walls 147, 157, 167, 177 of the respective second mold structures 142, 152, 162, 172, and the second mold structures 142, 152, 162, 172 are in contact with side walls 146, 156, 166, 176 of the respective first mold structures 141, 151, 161, 171.

Figure 15A:
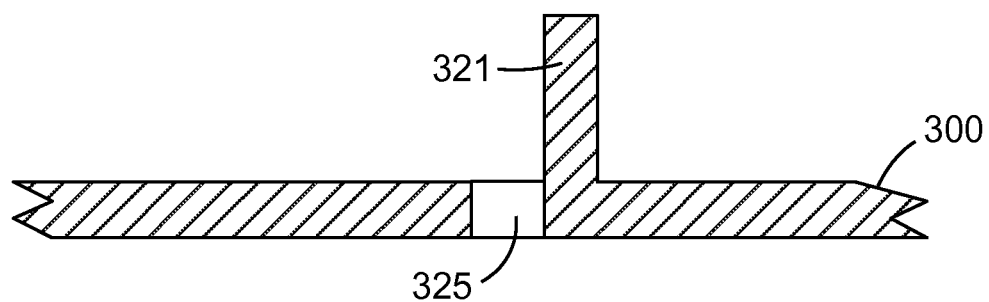
FIG. 15a is a cross-sectional view of a section of a blank or tray wall having a protrusion.
Figure 15B:
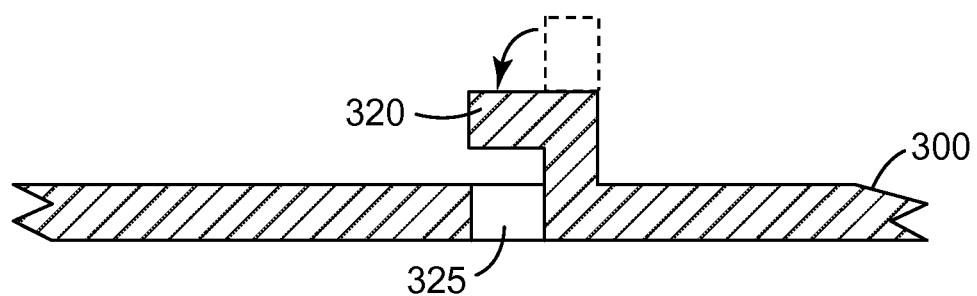

FIG. 15a shows a cross-sectional view of a section of a blank or a tray wall 300. The wall 300 comprises a passageway 325 and a protrusion 321 adjacent the passageway 325. The protrusion 321, for example, may be manufactured in one piece with the wall. In this embodiment the protrusion does not necessarily need to be arranged directly adjacent the passageway. In this embodiment "adjacent" may also be regarded as a distance the protrusion is spaced away from the passageway which still allows the protrusion to be deformed to form a retaining element overhanging the passageway. The protrusion initially may, as shown, not have an undercut, as this term is used within the scope of this invention. The protrusion 321 is deformed subsequent to manufacturing of the blank or tray so as to form a retaining element 320 (shown in FIG. 15b), which can be done by the application of heat, mechanical force, or the like.

Figure 16A:
FIGS. 16a-16d are cross-sectional views and a top view of a section of a blank or tray wall having a retaining element made by deformation of an area of the blank or tray wall.
Figure 16B:
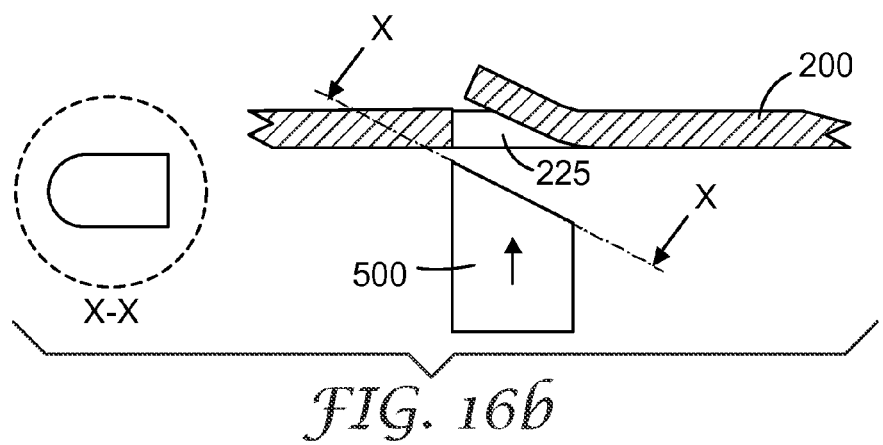
Figure 16C:
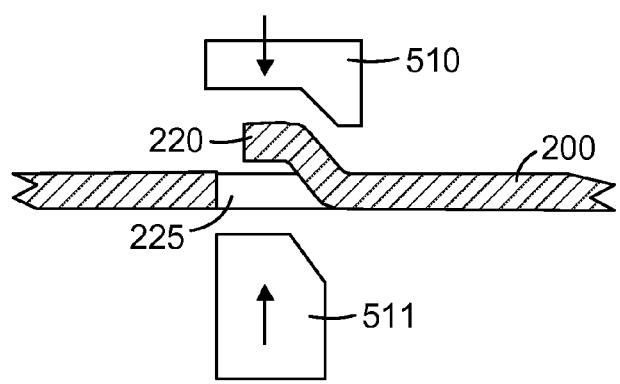
Figure 16D:
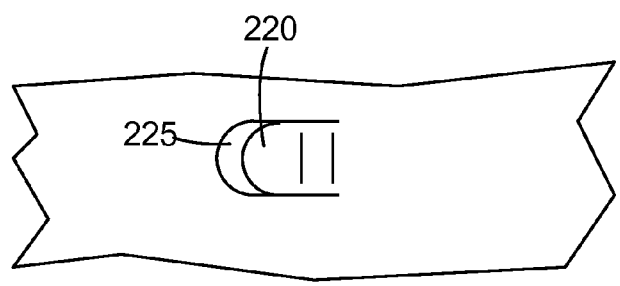

FIG. 16a shows a cross-sectional view of a section of a blank or a tray wall 200. In FIG. 16b the wall 200 comprises an incision, in this case along a generally U-shaped contour. Alternatively, the incision may have any other shape or may even be just I-shaped. A cutting tool 500 is shown, which has a cross-sectional shape as illustrated in view X-X. The cutting tool 500 has an inclined front face so that it gradually penetrates into the wall 200 and moves the area surrounded by the incision out of the plane of the remainder of the wall. Thereby the passageway 225 is formed. The cutting tool 500 is moved only partially into the wall 200 so that it does not completely cut a hole through to the other side, but rather creates a generally U-shaped incision. In a subsequent step, as shown in FIG. 16c, the area of the wall surrounded by the incision is formed by forming tools 510 and 511. The forming tools 510, 511 are adapted to be moved against one another so that they press the wall area from both sides and thereby deform it to form the final shape of the retaining element 220. Cutting and forming of the retaining element may be done in a single step. Further a subsequent or simultaneous forming of the retaining element may not be necessary in case a structure as shown in FIG. 16b is sufficient to serve as a retaining element. For example, if the incision is I-shaped, a subsequent forming of a retaining element may not be necessary. FIG. 16d shows a top view of the wall 200 showing the shape of the incision.

As shown, the passageways of all embodiments preferably extend substantially linearly. However, the passageways of all embodiments may also extend along a path that curves or bends. It is preferred that the passageways of all embodiments extend along a direction that is generally, perpendicular, and more preferably perpendicular relative to one of the wall surfaces. However, optionally the passageways extend along a direction that is inclined relative to one of the tray wall surfaces. The passageways of all embodiments may have a stepped or tapered structure, in which case the cross-sectional area of the passageways at the second wall surface (the wall surface farther from the retaining elements) is preferably greater than the cross-sectional area at the first wall surface (the wall surface closer to the retaining elements). The passageways of all embodiments may have at least over a part of their length a circular, oval, rectangular or any other suitable shape. Preferably, the passageways have a generally cylindrical, more preferably a cylindrical shape.

The present invention has now been described with reference to several embodiments thereof. It will be apparent to those skilled in the art that many changes can be made in the embodiments described without departing from the scope of the present invention. Thus the scope of the present invention should not be limited to the structures described in this application, but only by structures described by the language of the claims and the equivalents of those structures. The inventions also embraces embodiments not explicitly described before wherein such embodiments comprise features of different embodiments described above and claimed below.

We claim:

1. A dental impression tray having a wall forming a reservoir to receive a dental impression material, the tray comprising at least one retaining element at least partially overhanging an associated passageway, wherein the passageway forms at least a part of a channel through the wall, and wherein the passageway extends between a first wall surface and a second wall surface that face in different directions, the retaining element being adapted to anchor solidified dental impression material to the tray, and wherein the retaining element comprises a retaining surface spaced from and facing the passageway associated with the retaining element, and wherein the retaining surface protrudes from the first wall surface into the tray, such that in use the dental impression material flows around the retaining element and flows beneath the retaining surface to reach the passageway.

2. Dental impression tray according to claim 1, wherein the retaining element is formed in one piece with the wall.

3. Dental impression tray according to claim 1, wherein the retaining element comprises a base portion projecting from the first wall surface and a head portion projecting from the base portion.

4. Dental impression tray according to claim 3, wherein the retaining element comprises at least two base portions, and wherein the base portions and the head portion form a generally U-shaped bridge spanning the passageway associated with the retaining element.

5. Dental impression tray according to claim 3, wherein the head portion is inclined with respect to the base portion, and wherein the head portion with the base portion forms a hook, with the head portion at least partially overhanging the passageway associated with the retaining element.

6. Dental impression tray according to claim 1, wherein the base portion and the head portion of the retaining element are generally L-shaped, with the head portion at least partially overhanging the passageway that is associated with the retaining element.

7. Dental impression tray according to claim 6, wherein at least one of the base and the head portions comprises a cross-sectional area of between 0.25 mm² and 4 mm².

8. Dental impression tray according to claim 1, wherein the cross-sectional area of the passageway is in a range selected from between 0.5 and 10 mm², between 1 and 6 mm² and between 2 and 4 mm².

9. Dental impression tray according to claim 1, comprising a plurality of retaining elements each associated with a passageway.

10. Dental impression tray according to claim 1, wherein the tray is made of plastic.

11. Method of forming a dental impression tray of claim 1 having a reservoir bottom and at least one retaining element arranged within the reservoir at the reservoir bottom, wherein the tray is formed by one-shot injection molding.

12. Method of forming a dental impression tray according to claim 1 having a plurality of retaining elements.

13. Mold for forming a dental impression tray according to claim 1, comprising
  (i) a first mold piece having a first mold structure for forming
  the first wall surface of the tray wall;
  (ii) a second mold piece having a second mold structure for forming the passageway in the tray wall; wherein the first mold structure and the second mold structure are adapted to contact at a contact surface with one another when the first mold piece and the second mold pieces are positioned together.

14. A kit, comprising a dental impression tray according to claim 1, and a dental impression material.

15. Dental impression tray according to claim 1, wherein the retaining element and the associated passageway are shaped as crosses or the negative of crosses.

16. Dental impression tray according to claim 1, wherein the retaining element bridges the associated passageway.

17. Kit, comprising a plurality of dental impression trays, wherein the dental impression trays have different sizes adapted to fit a variety of clinical situations, at least one tray comprising a wall forming a reservoir to receive a dental impression material, the tray comprising at least one retaining element at least partially overhanging an associated passageway, wherein the passageway forms at least a part of a channel through the wall, and wherein the passageway extends between a first wall surface and a second wall surface that face in different directions, the retaining element being adapted to anchor the solidified dental impression material to the tray, and wherein the retaining element comprises a retaining surface spaced from and facing the passageway associated with the retaining element, and wherein the retaining surface protrudes from the first wall surface into the tray, such that in use the dental impression material flows around the retaining element and flows beneath the retaining surface to reach the passageway.

18. A dental impression tray having a wall forming a reservoir, the tray comprising at least one retaining element at least partially overhanging an associated passageway,
  wherein the passageway forms at least a part of a channel through the wall,
  wherein the passageway extends between a first wall surface and a second wall surface that face in different directions,
  wherein the retaining element comprises a retaining surface spaced from and facing the passageway,
  wherein the retaining surface protrudes from the first wall surface into the tray, and
  wherein the first wall surface is recessed relative to an inner wall of the tray.

* * * * *